United States Patent
Van Lente et al.

(10) Patent No.: US 6,376,252 B1
(45) Date of Patent: Apr. 23, 2002

(54) PREPARATION AND METHOD FOR CAT BOX FILLER ADDITIVE CAPABLE OF DETECTING FELINE LOWER URINARY TRACT DISEASE (FLUTD)

(75) Inventors: Michael A. Van Lente, Elkhart; Robert Bauer, Bristol; Carol J. Allen, Mishawaka, all of IN (US); Ronald A. Lewis, II, St. Louis; Glenn E. Gibson, Crestwood, both of MO (US)

(73) Assignees: Environmental Test Systems, Inc., Elkhart, IN (US); Golden Cat Division of Ralston Purina, St. Louis, MO (US)

( * ) Notice: Subject to any disclaimer, the term of this patent is extended or adjusted under 35 U.S.C. 154(b) by 0 days.

(21) Appl. No.: 09/377,647

(22) Filed: Aug. 19, 1999

(51) Int. Cl.⁷ .................... G01N 33/48; G01N 33/49; G01N 33/493

(52) U.S. Cl. .................... 436/66; 422/56; 422/61; 436/166; 436/177; 436/176; 436/169

(58) Field of Search .................... 422/56, 58, 61; 436/66, 169, 164, 166, 176, 177

(56) References Cited

U.S. PATENT DOCUMENTS

| | | | |
|---|---|---|---|
| 3,986,833 A | * 10/1976 | Mast et al. | 436/66 |
| 4,071,321 A | 1/1978 | Lam | 23/253 |
| 4,427,769 A | 1/1984 | Adlercreutz et al. | 435/7 |
| 4,562,043 A | * 12/1985 | Mennen et al. | 422/56 |
| 4,673,654 A | * 6/1987 | Talmage | 436/66 |
| 5,081,040 A | 1/1992 | Patel et al. | 436/66 |
| 5,468,450 A | 11/1995 | Michael | 422/56 |
| 5,780,385 A | 7/1998 | Santioemmo et al. | 502/401 |
| 5,830,765 A | 11/1998 | Santioemmo et al. | 436/66 |

FOREIGN PATENT DOCUMENTS

WO  WO 96/17245  6/1996

* cited by examiner

*Primary Examiner*—Lyle A. Alexander
(74) *Attorney, Agent, or Firm*—Barnes & Thornburg

(57) ABSTRACT

Test devices and methods are provided for detection of feline lower urinary tract disease. The test devices comprise a matrix impregnated with a color indicator and a stabilizer wherein the indicator remains stable when exposed to ambient conditions and wherein a positive color response remains stable for a sufficient time for the color response to be observed. The test devices may be provided for use in combination with conventional cat box filler.

17 Claims, No Drawings

PREPARATION AND METHOD FOR CAT BOX FILLER ADDITIVE CAPABLE OF DETECTING FELINE LOWER URINARY TRACT DISEASE (FLUTD)

FIELD OF THE INVENTION

This invention relates to test strips which may be used in pieces in combination with a bed of conventional cat box filler for detection of feline urinary tract disease.

BACKGROUND OF THE INVENTION

Feline lower urinary tract disease (FLUTD) can be a life-threatening condition for cats. In particular, the main problem that cat owners face with FLUTD is that the disease is life-threatening to the cat by the time the symptoms are noticeable to the owner. Crystals of magnesium ammonium phosphate (MAP) can precipitate in the cat's urinary tract and obstruct it. If left untreated, a "blocked" cat will die within days. Furthermore, treatment is costly and traumatic to the cat, to say nothing of the affect on the cat's owner. With early detection made possible by occult blood testing, cat owners could in theory successfully treat the problem of FLUTD simply by changing the cats' diets.

The major problem for early detection of FLUTD is that the cat owners are unsophisticated in detecting the symptoms. With the symptoms going unrecognized, often by the time the pet owner takes the cat to the veterinarian, it is simply too late.

While detection systems are available for FLUTD that rely upon occult blood testing of urine, it is a fact that it is difficult to conduct the test or even when to know one needs to conduct the test. One easy answer is to provide the test material in the cat box filler in which the cats normally urinate.

However, providing a reliable occult blood detection system in cat box filler itself has its own problems. For example, the test indicator material must be stable when exposed to a wide variety of ambient conditions varying from extremely dry, to extremely humid, all over a wide range of temperatures. Often such stability is very difficult to achieve.

Another common problem with normal test indicators is that pet owners are insufficiently observant to notice a color change before the color indicator decays. Thus a reliable indicator should stay at the changed color for a period of at least 8 hours in order for the pet owner to have a sufficient chance to observe the color change.

Another problem often occurring with test reagents mixed with the cat box filler is that the cat's sensitive sense of smell will detect any odor changes, making the cat shy away from the litter. Thus any test reagent which can be successfully mixed with cat box filler must be provided in a substantially inoffensive odor form for the cats.

Yet another common problem which must be overcome is providing a cat box filler/test reagent combination which has shelf life stability such that it can be stored in merchandisable containers for a sufficient period of time to allow transport, shelf display, purchase, and then use.

Previously-used materials and systems for detection of FLUTD have involved one or more of the above deficiencies. It is a primary object of the present invention to overcome these deficiencies with a material and system which can accurately test for FLUTD and which can be safely and reliably stored, transported, and ultimately used by the pet owner.

In particular, it is one object of this invention to provide test strip materials which can be subdivided into pieces and then conveniently homogeneously mixed with conventional cat box filler to provide a safe and reliable occult blood test for FLUTD.

Another objective of the present invention is to provide test strip materials which can be combined with cat box filler which exude only odors that are nonoffensive to the cat.

Yet another objective of the present invention is to provide a test composition which can be mixed with conventional cat box filler and still show adequate stability towards changing weather and light conditions.

An even further objective is to provide a FLUTD test composition which can be triggered for test by as few as 100 red blood cells per microliter of cat urine.

A yet further objective is to provide a litter additive composition which has a pink color in the unreacted form, since such color is found pleasing to the pet owner.

The method and manner of accomplishing each of the above objectives will become apparent from the detailed description of the invention which follows.

SUMMARY OF THE INVENTION

Test strips for detection of feline lower urinary tract disease (FLUTD) which remain stable when exposed to ambient conditions, and which provide a positive color response for at least 8 hours, are provided for use in combination with conventional cat box filler.

DETAILED DESCRIPTION OF THE INVENTION

Conventional cat box filler is typically a clay product, often having an off-white, grayish color. Such processed granular clay materials are often montmorrillonite clays, and are well known and conventionally available. The test strip materials of the present invention are designed to be cut in small pieces approximately the size of the cat box filler material so they can be easily admixed therewith without interfering with the cat's natural attraction to its litter filled cat box.

The test strip material in its simplest form is a piece of bibulous filter paper matrix of sufficient porosity and capillary affinity to cause a urinary sample from the cat to migrate into the test paper, which is coated with the test reagent. The paper matrix may be a woven or a non-woven material and may include, but is not limited to cellulosic natural fiber materials of the type normally used to make filter papers, etc. Suitable matrixes or substrate papers are available under the trademarks Gelok 3001 S/S laminate, Hollingsworth and Vose 7303 (a polyester); Walkisoft FG400 (superabsorbent paper used in diapers); Whatman 3MM; Whatman CCP500; and Ahlstrom 237. Other natural or synthetic fiber matrix materials, either woven or non-woven, may also be used, such as organic polymer materials. Satisfactory results are achieved with Ahlstrom 237, as illustrated in the examples below.

In accordance with the process of the present invention, pieces of bibulous paper are initially impregnated in a first reagent dip with aqueous components. The aqueous component composition will typically comprise a surfactant, a buffer, and preferably a color enhancer and a color stabilizer. Conventional aqueous buffers are well known and can include, for example, malonic acid and tris(hydroxymethyl) aminomethane or other conventional aqueous buffers. The buffer should be present in an amount sufficient to provide a pH within the range of about 5.5 to about 6.5, most preferably 5.9 to 6.1, and performance seems best at a buffer pH of 6.0.

A suitable surfactant can be added in order to enhance wetting with the later used organic materials. It can include conventional natural or synthetic detergents. Suitable results are obtained with sodium lauryl sulfate, for example.

Where sodium lauryl sulfate, the preferred surfactant, is used, it is preferably at a concentration of from 2 to 20 grams per liter, preferably at about 10 grams per liter. For the buffer, if the buffer is malonic acid it is preferably at a concentration of 13 to 26 grams per liter, and preferably at 13 to 14 grams per liter, assuming a pH of 6.0. The buffer may contain tris(hydroxymethyl)amino methane within a range of 12.1 to 25.0 grams per liter, preferably 11.5 to 12.5 grams per liter.

As previously explained, in the preferred embodiment the buffer also contains an enhancer for color. A suitable enhancer is quinoline at a concentration of from 1 to 30 grams per liter, preferably 14 to 15 grams per liter. Also, as an enhancer, one can use isoquinoline-5-sulfonic acid (IQS) at a level of 8 to 30 grams per liter, preferably about 24 grams per liter.

After the bibulous paper matrix is impregnated with the aqueous solution, it is then dried. It may be air-dried or oven-dried. Once the paper is dry, it is then ready for impregnation with organic components which include the preservative, an oxidant and the occult blood indicator.

As should be apparent, the matrix system is more responsive to the organic-based system because of the wetting surfactant, now present in the first dip materials already dried upon the matrix. However, the first and second dips can be reversed, if desired.

Indicators which have a noticeable color change when wetted with cat urine having occult blood include but are not limited to guaiac, benzidine, ortho-tolidine, ortho-dianisidine, or other "leuco-dyes" which turn various shades and intensities of blue in the presence of occult blood, hemoglobin or other peroxidase-containing blood components.

The most preferred are tetramethylbenzidine such as 3,3',5,5'-tetramethylbenzidine. Where this is employed, it should be at a level of 1 to 15 grams per liter, preferably 1.5 to 2.5 grams per liter. The preferred tetramethylbenzidine derivatives generally should have a formula of:

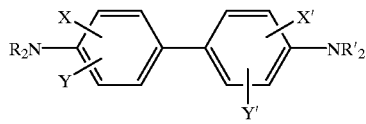

where X, X', Y and Y' and R and R' are hydrogen or the most preferred alkyl group of up to six carbon atoms and may be the same or different. Preferably the alkyl group contains four or less carbon atoms. Benzidine type compounds such as 3,3',5,5', tetramethylbenzidine, o-tolidine, o-dianisidine, N,N,N',N', tetramethylbenzidine, and the like may be used. 3,3',5,5', tetramethylbenzidine is the preferable compound for use in the present composition.

The organic phase based system may also contain an oxidant which can be cumene hydroperoxide or, for example, diisopropylbenzene dihydroperoxide (DBDH).

Because the color change of occult blood indicators such as tetramethylbenzidine (3,3',5,5', tetramethylbenzidine) fade over time, it is desirable that the system have preservatives such as BHT to preclude unwanted color change before exposure to blood/urine mixtures. This will allow the color to last at least for an 8-hour period. This gives the pet owner sufficient time to notice the color change in the kitty litter box. Butylated hydroxytoluene (BHT) can be a suitable preservative.

The level of occult blood indicator, if it is 3,3'5,5'-tetramethylbenzidine, should be from 1 to 15 grams per liter, preferably 1.5 to 2.5 grams per liter. Preferably the organic phase portion of the dip should also contain a dye such as Acid Red 106 at a range of 8 to 15 mg/l, preferably about 11.5 mg/l. This allows the strips to have the preferred pink color.

The test paper now dried from the first step is impregnated with the second strip solution which may contain as a basic organic solvent ethyl acetate. Because of the wetting agent, one can be assured that any cat urine will wet the reagent paper. The amount of time in the second strip solution should be sufficient to saturate it, perhaps five seconds, but generally within range 3 seconds to 60 seconds.

The amount of time in the first strip or paper solution can also be sufficient for saturation of the matrix.

Once the strips or pieces of matrix test paper are dried, for the second dip they are then cut in sizes and shapes (diamond shape is satisfactory), such that they can be homogeneously admixed with the kitty filler in the cat's litter box.

The buffered matrix pieces, now cut, may be sealed in a foil package of conventional construction, and sold. They will have a shelf life in the sealed container of at least several months, even from 12 months to 18 months. After they are opened, they will be admixed by the pet owner with the cat box filler material and placed in the cat's box. If the cat is suffering from FLUTD, the urine will be deposited on the test pieces which will change from their naturally-occurring pink color to a blue, and maintain that color for at least an 8-hour period. As a result, the pet owner is warned of problems that should signal the need for a visit to the veterinarian.

The color change observed on these strips or matrix pieces in tests has been indicated as stable and does not have a tendency to photo-oxidize upon exposure to light since there is a preservative/anti-oxidant system.

Tests reveal that the composition as herein described can detect red blood cells at a level of 100 per microliter.

As can be seen from the above description and described tests, the invention achieves at least all of its stated objectives.

What is claimed is:

1. A method of detecting cats that suffer from feline lower urinary tract disease, which method comprises:

mixing with conventional cat box filler pieces of bibulous paper of such a size that the pieces can be easily mixed with the cat box filler, said pieces having been impregnated with an aqueous-based stabilizer component comprising 5-isoquinoline sulfonic acid and said pieces having been impregnated with a color indicator which will responsively change color in the presence of blood in cat urine; and thereafter observing the cat litter box to determine whether there is a color change from pink to blue.

2. In combination, cat box filler and pieces of test matrix for detection of feline lower urinary tract disease, the test matrix remaining stable when exposed to ambient conditions for several day and providing a positive color response that does not deteriorate significantly for at least 8 hours subsequent to exposure to urine having occult blood, comprising:

pieces of bibulous paper matrix of a size such that the pieces can be inconspicuously mixed with the cat box filler;

said pieces having been impregnated with an aqueous-based group of stabilizer components comprising 5-isoquinoline sulfonic acid; and said pieces having been impregnated with a color indicator that responsively changes color in the presence of blood in cat urine.

3. A test device for the detection of feline lower urinary tract disease comprising:

pieces of bibulous filter paper sized for mixing with cat box filler, said pieces having been impregnated with an aqueous-based stabilizer solution comprising a color enhancer, the color enhancer including 5-isoquinoline sulfonic acid, said pieces also having been impregnated with an indicator solution comprising a color indicator that responsively changes color in the presence of blood in cat urine, wherein said test device remains stable when exposed to ambient conditions for several days and provides a positive color response that will not deteriorate significantly for a period of 8 hours subsequent to exposure to urine.

4. The test device of claim 3 further having a capability of detecting at least 100 red blood cells per microliter in cat urine.

5. The test device of claim 3 in combination with conventional clay-based cat box filler.

6. The test device of claim 3 wherein the aqueous-based stabilizer solution further comprises a buffer, a surfactant, and an ambient condition stabilizer.

7. The test device of claim 6 wherein the buffer is provided in an amount sufficient to provide a pH within the range of 5.5 to 6.5.

8. The test device of claim 7 wherein the buffer is provided in an amount sufficient to provide a pH within the range of 5.9 to 6.1.

9. The test device of claim 8 wherein the buffer is provided in an amount sufficient to provide a pH of about 6.0.

10. The test device of claim 3 wherein the color enhancer further includes quinoline.

11. The test device of claim 3 wherein the indicator solution further comprises a preservative and an oxidant.

12. The test device of claim 11 wherein the preservative is BHT.

13. The test device of claim 11 wherein the oxidant is selected from the group consisting of cumene hyproperoxide and diisopropylbenzene dihydroperodide.

14. The test device of claim 3 wherein the indicator is a compound derived from benzidine.

15. The test device of claim 14 where the indicator is 3,3', 5,5', tetramethylbenzidine.

16. The test device of claim 3 provided in combination with a clay-based cat box filler subdivided to a size that is homogeneous with the sized pieces of bibulous filter paper.

17. The test device of claim 3 wherein the pieces of bibulous filter paper are packaged in a sealed foil container.

* * * * *